United States Patent [19]

Ljungberg

[11] Patent Number: 5,044,041
[45] Date of Patent: Sep. 3, 1991

[54] TOOTH CLEANER AND METHOD FOR THE MANUFACTURE THEREOF

[76] Inventor: Mats Ljungberg, Kryssgränd 4, Skåre, S-23100 Trelleborg, Sweden

[21] Appl. No.: 263,791

[22] PCT Filed: Apr. 21, 1987

[86] PCT No.: PCT/SE87/00202

§ 371 Date: Oct. 20, 1988

§ 102(e) Date: Oct. 20, 1988

[87] PCT Pub. No.: WO87/06452

PCT Pub. Date: Nov. 5, 1987

[30] Foreign Application Priority Data

Apr. 21, 1986 [SE] Sweden .................. 8601814

[51] Int. Cl.⁵ .................................. A47K 7/00
[52] U.S. Cl. .................. 15/210 R; 15/167.1; 15/159 A; 132/321; 132/329; 300/21
[58] Field of Search ............... 15/111, 159 A, 160, 15/167.1, 167.2, 189, 210 R, 118, 186–188, 211; 300/21; 433/141, 142; 132/321, 329

[56] References Cited

U.S. PATENT DOCUMENTS

| | | | |
|---|---|---|---|
| 1,470,710 | 10/1923 | Davis | 15/210 R |
| 1,526,267 | 2/1925 | Dessau | 15/188 |
| 1,604,731 | 10/1926 | Whittaker | 15/210 R |
| 2,171,591 | 9/1939 | Minich | 15/188 |
| 2,548,255 | 4/1951 | Gressler | 15/167.1 |
| 3,337,893 | 8/1967 | Fine et al. | 15/210 R |
| 3,939,520 | 2/1976 | Axelsson | 15/167.1 |

FOREIGN PATENT DOCUMENTS

| | | | |
|---|---|---|---|
| PCT/AK84/-00059 | 6/1984 | Denmark . | |
| 150785 | 8/1985 | European Pat. Off. | 15/167.1 |
| 2907667 | 9/1979 | Fed. Rep. of Germany | 300/21 |
| 3628722 | 2/1988 | Fed. Rep. of Germany | 15/167.1 |
| 508200 | 2/1956 | Italy | 15/167.2 |
| 82/01126 | 4/1982 | PCT Int'l Appl. | 132/329 |
| 86/02823 | 5/1986 | PCT Int'l Appl. | 132/329 |
| 425141 | 9/1982 | Sweden . | |
| 550229 | 12/1942 | United Kingdom | 300/21 |
| 2216427 | 10/1989 | United Kingdom | 132/321 |

*Primary Examiner*—Harvey C. Hornsby
*Assistant Examiner*—Mark Spisich
*Attorney, Agent, or Firm*—Merchant, Gould, Smith, Edell, Welter & Schmidt

[57] ABSTRACT

A tooth cleaner comprises an elongate plastic body (1) and a brush portion (2) connected with the body and consisting of a plastic fabric or net which forms bristles (3) projecting from the body in the transverse direction. A method for manufacturing the tooth cleaner comprises preparing an injection mould suited for injection moulding or like moulding of an elongate plastic body, inserting between the splits of the mould a strip of a plastic fabric or net having a larger width than the moulding cavity, closing the mould, and injecting plastic in the mould to form the body which is thermally bonded to the strip.

5 Claims, 2 Drawing Sheets

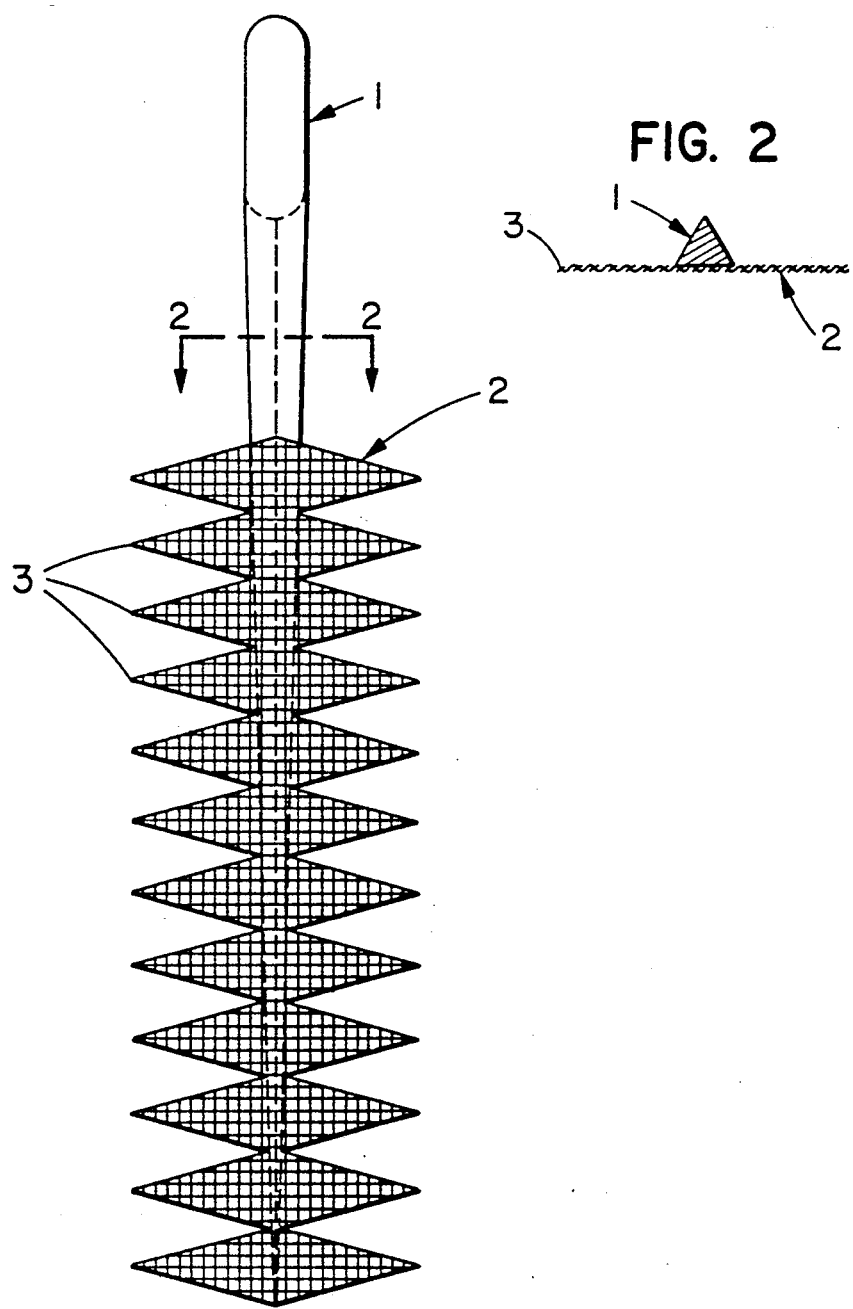

TOOTH CLEANER AND METHOD FOR THE MANUFACTURE THEREOF

The present invention relates to a tooth cleaner and a method for the manufacture thereof.

Conventional tooth cleaners, in most cases of wood, are not particularly effective, mainly because they are rigid, for which reason their edges or lateral surfaces cannot follow the shape of the tooth or teeth, when the cleaner is moved backward and forward in the space between two teeth. More often than not, such cleaning therefore requires supplementary floss treatment. Wooden tooth cleaners frequently break off cross-wise. There also exist plastic tooth cleaners with a handle and laterally projecting bristles integrally formed therewith. Due to the moulding technique employed, the bristles cannot be made in a sufficient number to achieve effective tooth cleaning, and they are of necessity too thick and feel disagreeable to the gums.

One object of the invention is to solve these problems by providing a flexible and effective tooth cleaner. A further object is to provide a quick and effective method for manufacturing the tooth cleaner.

According to the invention, these objects are achieved by a tooth cleaner and a method as claimed in the claims.

One embodiment of the invention will be described below, reference being has to the enclosed FIGS. 1 and 2 which depict a plan view of the view of the embodiment (FIG. 1) and a cross-sectional view of the embodiment depicted in FIG. 1 taken along line 2—2 (FIG. 2).

BRIEF DESCRIPTION OF THE DRAWINGS

FIG. 1 is a plan view of the tooth cleaner.

FIG. 2 is a cross-section through section 2—2 of FIG. 1.

Figure 3:
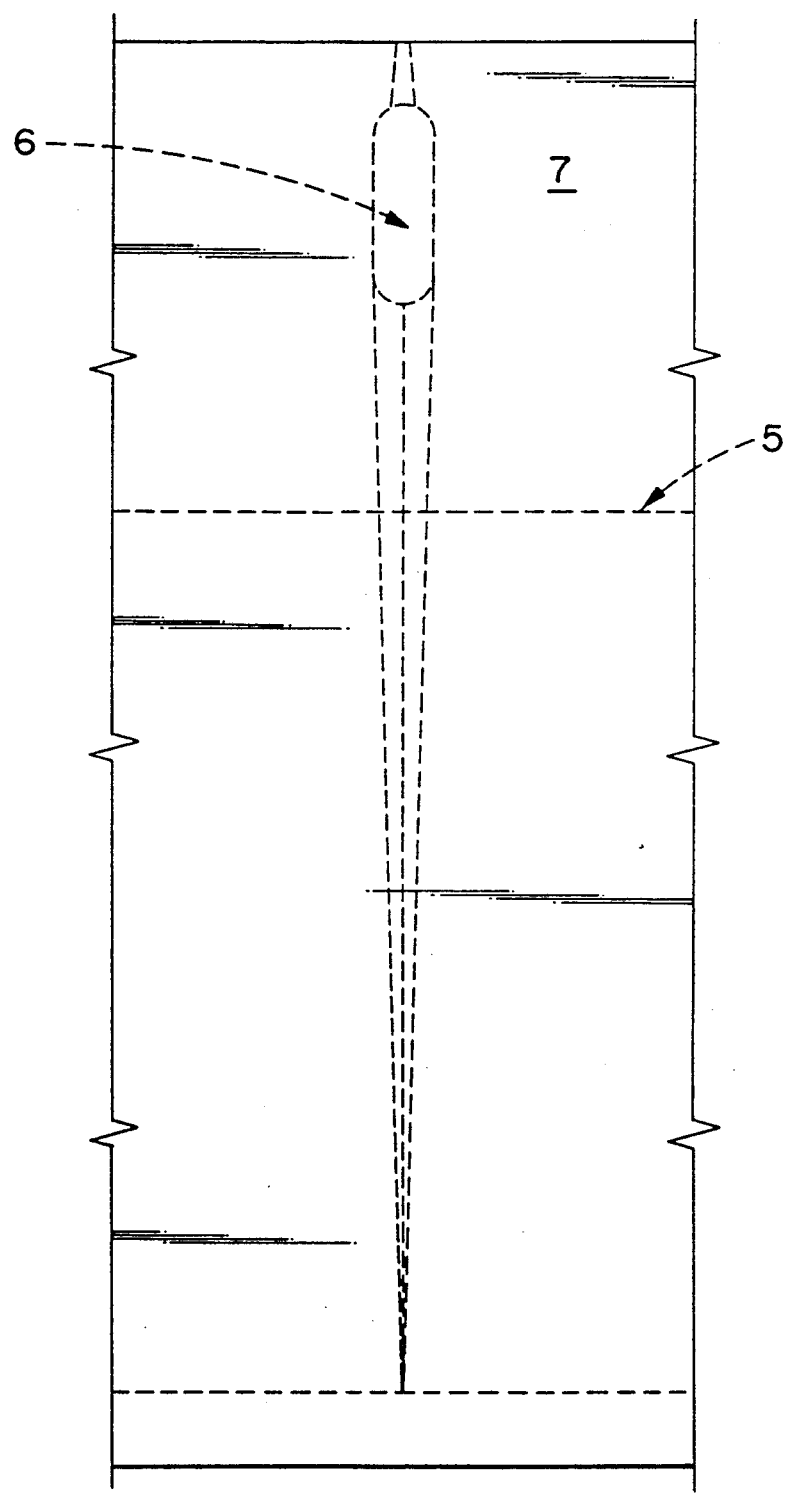
FIG. 3 illustrates the method of making the tooth cleaner of FIG. 1.

The cleaner is composed of an elongate, slightly flexible and slightly resilient thermoplastic body 1 which is triangular in cross-section and tapers to a point, and of a thermoplastic brush portion 2 which is attached to the base of the body 1 and comprises bristles 3 projecting from both sides of the body in the transverse direction thereof. The brush portion 2 covers a substantial part of the length of the body.

In the embodiment illustrated, the bristles 3 are formed of a silk-screen cloth available on the market, which has been punched so as to obtain the triangular bristle shape shown in the drawing. Polypropylene may be used for the body, and the silk-screen cloth here consists of nylon.

In a modification, the bristles can be formed of the nonwoven warp of a piece of woven fabric or net. In a further modification, the bristles are simply formed of the punched or cut long-side edges of a rectangular strip of fabric or net.

Referring to FIG. 3, a method is shown for manufacturing the tooth cleaner comprises inserting between the splits of a mould 7 suited for injection moulding of the body, a strip of a plastic fabric or not 5 so as to cover the part of the body moulding cavity 6, which is to form the bristle-carrying portion of the tooth cleaner, closing the mould and moulding the body, the strip being thermally bonded to the body. In a actual practice, a number of tooth cleaners are, of course, manufactured at the same time in one and the same mould with a plurality of body cavities, a strip of fabric (net) which is common to the bodies being cut or punched after moulding and stripping, so as to provide a plurality of tooth cleaners. Alternatively, the mould may be provided with cutting dies.

It will appreciated that the invention provides for varying degrees of softness or rigidity of the bristles.

I claim:

1. A tooth cleaner, characterized in that it comprises an elongate thermoplastic body which is substantially triangular in cross-section, and a brush portion (2) connected with said body which are adapted to fit in and clean the space between two teeth, said brush portion consisting of a strip of a thermoplastic material, said strip of thermoplastic material being fused to one side surface of said triangular body portion and extending at least slightly beyond said body in opposite transverse directions thereof, said strip also being coplanar with the side surface to which it is fused, said strip forming bristles along each oppositely extending portion, and further wherein said strip and bristles extend lengthwise along said body.

2. A tooth cleaner as claimed in claim 1, characterized in that the bristles of the brush portion have been provided by punching or cutting a strip of fabric or net.

3. A tooth cleaner as claimed in claim 1, characterized in that the bristles of the brush portion are formed of non-woven warp.

4. A tooth cleaner as claimed in claim 1, characterized in that said body (1) and said brush portion (2) consist of different thermoplastic materials which are thermally interconnected.

5. A method for manufacturing the tooth cleaner as claimed in claim 1, characterized by preparing an injection mould which is suitable for injection molding or like molding of an elongate plastic body, inserting between the splits of said mold a strip of a plastic fabric or net so as to over the part of the body cavity, which is to form the tooth cleaner portion carrying the bristles, closing the mould, and injecting plastic into the cavity to form said body which is thermally bonded along one side of said body to said strip.

* * * * *

UNITED STATES PATENT AND TRADEMARK OFFICE
CERTIFICATE OF CORRECTION

PATENT NO. : 5,044,041  Page 1 of 3

DATED : September 3, 1991

INVENTOR(S) : Mats Ljungberg

It is certified that error appears in the above-identified patent and that said Letters Patent is hereby corrected as shown below:

In Column 1, line 17,
 please delete "moulding" and substitute therefore--molding--.

In Column 1, line 29,
 please delete "has" after the word "being" and insert --had--

In Column 2, line 3,
 please delete "is shown" after the word "Method".

In Column 2, line 5,
 please delete "mould" and substitute therefore--mold--.

In Column 2, line 5,
 please delete "moulding" and substitute therefore--molding--.

In Column 2, line 7,
 please delete "moulding" and substitute therefore--molding--.

In Column 2, line 6,
 please delete "not" and substitute therefore-net--.

In Column 2, line 9,
 please delete "mould" and substitute therefore--mold--.

UNITED STATES PATENT AND TRADEMARK OFFICE
CERTIFICATE OF CORRECTION

PATENT NO. : 5,044,041

DATED : September 3, 1991

INVENTOR(S) : Mats Ljungberg

It is certified that error appears in the above-identified patent and that said Letters Patent is hereby corrected as shown below:

In Column 2, line 9,
  please delete "moulding" and substitute therefore--molding--.

In Column 2, line 10,
  please delete "a" after the word "in".

In Column 2, line 12,
  please delete "mould" and substitute therefore--mold--.

In Column 2, line 14,
  please delete "moulding" and substitute therefore--molding--.

In Column 2, line 16,
  please delete "mould" and substitute therefore--mold--.

In Column 2, claim 5, line 48,
  please delete "mould" and substitute therefore--mold--.

In Column 2, claim 5, line 51,
  please delete "over" and substitute therefore--cover--.

UNITED STATES PATENT AND TRADEMARK OFFICE
CERTIFICATE OF CORRECTION

PATENT NO. : 5,044,041

DATED : September 3, 1991

INVENTOR(S) : Mats Ljungberg

It is certified that error appears in the above-identified patent and that said Letters Patent is hereby corrected as shown below:

In Column 2, claim 5, line 53, please delete "mould" and substitute therefore --mold--.

Signed and Sealed this

Twenty-fifth Day of May, 1993

Attest:

MICHAEL K. KIRK

*Attesting Officer*    Acting Commissioner of Patents and Trademarks